United States Patent [19]

Abrams et al.

[11] Patent Number: 5,072,011
[45] Date of Patent: Dec. 10, 1991

[54] PT(IV) COMPLEXES

[75] Inventors: Michael J. Abrams, Glenmore; Christen Giandomenico, Exton, both of Pa.; Barry A. Murrer, Reading, Great Britain; Jean F. Vollano, Exton, Pa.

[73] Assignee: Johnson Matthey, Inc., Valley Forge, Pa.

[21] Appl. No.: 602,931

[22] Filed: Oct. 25, 1990

Related U.S. Application Data

[63] Continuation of Ser. No. 296,776, Jan. 13, 1989, abandoned, which is a continuation-in-part of Ser. No. 151,674, Feb. 2, 1988, abandoned.

[51] Int. Cl.$^5$ ..................... C07F 15/00; A61K 31/295
[52] U.S. Cl. ................................................. 556/137
[58] Field of Search ................... 556/40, 137; 514/492

[56] References Cited

U.S. PATENT DOCUMENTS 4,466,924  8/1981  Verbeek et al. .................... 556/137

FOREIGN PATENT DOCUMENTS 0237450  9/1987  European Pat. Off. .
2148891  6/1985  United Kingdom .

OTHER PUBLICATIONS

Tobe & Khokhar, *J. Clin. Hemotol. et. Oncol.* 7(1) 113–134, pp. 130–134.

Hall et al., *Journal of Clinical Hemotology and Oncology*, 7(1):231–241 (1977).
Maeda et al., *Jpn. J. Cancer Res.*, 77(6):523–525 (1986).
J. Blanchard, *Am. J. Pharm.*, 135–146 (1975).
M. Orme, *Br. J. Anaesth*, 56, 59 (1984).
Brandon et al., *J. Med. Chem.*, 27:861 (1984).
Cleare et al., *Plat. Met. Rev.*, 17:2 (1973).
Braddock et al., *Chem. Biol. Interact.*, 11:145 (1975).
Cowens et al., *Int. J. of Mass Spectrometry & Ion Physics*, 48:177–180 (1983).

*Primary Examiner*—Gary P. Straub
*Assistant Examiner*—Stuart L. Hendrickson
*Attorney, Agent, or Firm*—Cushman, Darby & Cushman

[57] ABSTRACT

A Pt(IV) complex of the formula

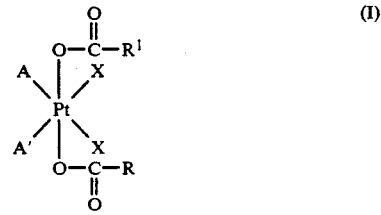

wherein A and A' are $NH_3$ or an amino group; R and R' are hydrogen, alkyl, alkenyl, aryl, aralkyl, alkylamino or alkoxy or functionalized derivatives thereof; and X is halogen or alkyl mono- or dicarboxylate. The complexes have high antitumor activity, particularly when administered orally.

6 Claims, No Drawings

PT(IV) COMPLEXES

This is a continuation of application Ser. No. 07/296,776, filed on Jan. 13, 1989, which was abandoned upon the filing hereof which is a continuation-in-part of Ser. No. 151,674 filed Feb. 2, 1988, now abandoned.

The present invention relates to novel Pt(IV) complexes which demonstrate potent antitumor activity.

BACKGROUND OF THE INVENTION

Since the development and use of cis-platin as an effective anti-tumor agent, extensive research has been directed towards finding platinum complexes which might demonstrate similar or better antitumor activity while providing improvements in other properties, e.g., reduced toxicity or other undesired side effects.

A variety of cis-platin analogs have been extensively investigated, including complexes of Pt(IV) such as cis-trans-cis-$PtCl_2(OH)_2(i-prNH_2)_2$ (U.S. Pat. No. 4,394,319) and $PtCl_4$(DACH) (U.S. Pat. No. 4,550,187). Most Pt antitumor compounds described to date are hydrophilic in that they dissolve more readily in water than they do in common organic solvents, e.g., acetone, methylene chloride, etc. Examples of such hydrophilic complexes include cis-platin itself and carboplatin. Recently, a variety of liposoluble Pt complexes have been reported (e.g., bis(caprato) DACH Pt) that are poorly soluble in water but readily dissolved in organic solvents. See Maeda et al., JPN, J. Cancer Res. 77, 523-525 (1986).

Certain 1-amino-2-aminomethylcyclopentane platinum (II) and (IV) complexes have also been described in U.S. Pat. No. 4,466,924. This patent refers generally to the possibility of including acetate, oxalate, malonate or carboxylate substituents attached to the Pt atom. However, no specific examples of such complexes are given in the patent.

DESCRIPTION OF THE INVENTION

The present invention provides Pt(IV) complexes which demonstrate a high degree of antitumor activity, particularly when orally administered. Many of these complexes exhibit a high degree of solubility in both water and organic solvents and this dual-type solubility property may contribute significantly to the high degree of antitumor activity demonstrated by these complexes when given orally. See J. Blanchard, *Am. J. Pharm.*, 135 (1975) and M. Orme, *Br. J. Amaesth.*, 56, 59 (1984).

The complexes of the invention may be structurally illustrated by Formula I as follows:

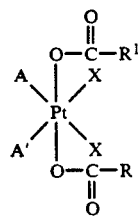
(I)

where A and A' are $NH_3$ or amino, e.g., a $C_1$-$C_{10}$ alkyl amine (straight chain, branched or cyclic); R and $R^1$ are selected from the group consisting of hydrogen, alkyl, e.g., $C_1$-$C_{10}$ alkyl, alkenyl, aryl, aralkyl, alkylamino or alkoxy or functionalized derivatives thereof; and X is selected from the group consisting of halogen or alkyl mono- or di-carboxylate.

The A and A' substituents may be the same or different. In the simplest embodiment, both A and A' may be $NH_3$. However, one or both of these substituents may be an amine, the nature of which can be widely varied. This includes, for example, aromatic, heteroaromatic or heterocyclic radicals, e.g., anilino, pyridyl, aziridine or morpholine groups, functionalized amines such as $NH_2(CH_2)_3CO_2C_2H_5$; $X^1CO_2$-c-$C_6H_{10}CH_2NH_2$, $X^1CO_2CH_2CH_2NH_2$ or the like where $X^1$ is a lower alkyl such as methyl, ethyl, propyl, etc. A and/or A' may also be a chelating diamine such as 1,2-diaminocyclohexane (DACH) or 2-aminomethylcyclohexylamine (AMCHA). It will be understood that when a chelating amine is used, A and A' are joined together to complete a ring provided, however, that A and A' do not include a cyclopentane ring when R and/or $R^1$ are methyl.

As other specific examples of A and/or A', there may be mentioned primary or secondary amines such as n-propylamine (n-$C_3H_7NH_2$), isopropylamine (i-$C_3H_7NH_2$), cyclopropylamine (c-$C_3H_5NH_2$), cyclobutylamine (c-$C_4H_7NH_2$), isobutylamine (i-$C_4H_9NH_2$), tertiary butylamine (t-$C_4H_9NH_2$), neo-pentylamine, tert-amylamine, isoamylamine (i-$C_5H_{11}NH_2$), cyclopentylamine (c-$C_5H_9NH_2$), cyclohexylamine (c-$C_6H_{11}NH_2$), cycloheptylamine (c-$C_7H_{13}NH_2$) and the corresponding secondary alkylamines, e.g., di-n-propylamine. As will be evident, the alkyl group or groups in the alkyl amine may be straight chain, branched chain or cyclic. Mixed alkyl amine groups are also contemplated.

The R and $R^1$ substituents may also be the same or different. Representative values for the R and $R^1$ substituents include alkyl of 1-10 carbons, straight or branched chain such as $CH_3$, $C_2H_5$, n-$C_3H_7$, i-$C_3H_7$, n-$C_4H_9$, t-$C_4H_9$, i-$C_4H_9$, n-$C_5H_{11}$, n-$C_6H_{13}$ or n-$C_7H_{15}$; cycloalkyl of 3-7 carbons such as cyclopropyl, cyclobutyl, cyclopentyl, cyclohexyl or cycloheptyl; ethenyl, propenyl or other alkenyl; phenyl, tolyl, naphthyl or similar monocyclic or dicyclic aryl; benzyl or phenethyl or like aralkyl; lower alkylamino (primary amino) of up to 6 carbons, e.g., methylamino ($CH_3NH-$), ethylamino ($C_2H_5NH-$); and lower alkoxy of 1-6 carbons such as methoxy, ethoxy, etc. R and $R^1$ may also be a functionalized group such as an alkoxy alkyl (e.g., methoxy-methyl), tosylamino or the like. The definition of R and $R^1$ as given above for Formula I is intended to include such functionalized or substituted groups.

Representative of the X substituents are Cl, Br or other halogen, or $C_1$-$C_4$ alkyl mono-carboxylate such as acetate or di-carboxylate such as malonate or cyclobutane-1,1-dicarboxylate. The X substituents, like the R, $R^1$ and A/A' substituents, may be the same or different. They may also be combined in the form of a chelating dicarboxylate radical.

It will be appreciated that the indicated substituents for A, A', X, R and $R^1$ may themselves be substituted. For example, when R and/or $R^1$ are alkyl, the alkyl may be substituted with halogen to provide a chloromethyl substituent.

A preferred subgroup of compounds within Formula (I) are those wherein A is $NH_3$, A' is lower alkyl ($C_1$-$C_7$)amino, X is chlorine and R and $R^1$ are lower alkyl ($C_1$-$C_7$) or cycloalkyl of 3-7 carbons. Especially preferred are such compounds wherein A' is cyclopentylamine (c-C$_5$H$_9$NH$_2$) or cyclohexylamine (c-C$_6$H$_{11}$NH$_2$) and R and R$^1$ are both propyl.

Other subgroups of compounds within Formula (I) include those wherein A is NH$_3$, A' is alkylamino, X is chlorine and R and R$^1$ are lower alkylamino or lower alkoxy.

The compounds of the invention and the starting materials necessary therefor may be prepared by procedures generally known in the art. Starting compounds of the type Pt(OH)$_2$ Cl$_2$ AA' and Pt(OH)$_2$Cl$_2$ A$_2$ are conveniently prepared by the reaction of H$_2$O$_2$ with the corresponding Pt(II) dichloro species (R. J. Brandon, J. C. Dabrowiak, *J. Med. Chem.*, 27:861 (1984)). The synthesis of the Pt(II) dichloro species is described in the literature (see, M. J. Cleare, J. D. Hoeschele, *Plat. Met. Rev.*, 17:2 (1973) and T. A. Connors et al., *Chem. Biol. Interact.*, 11:145 (1975). For example, the complexes where X is halogen, may be prepared by reacting a compound Pt(OH)$_2$X$_2$ A,A', e.g., Pt(OH$_2$)Cl$_2$ (i-PrNH$_2$)$_2$, with the appropriate anhydride, isocyanate or pyrocarbonate. The reaction may be carried out by simply mixing the reactants together at room temperature (20°-25° C.), then chilling to crystallize out the desired product. A generally similar preparation of other Pt complexes of the formula PtCl$_2$(RCO$_2$)$_2$(i-PrNH$_2$)$_2$ where R is CF$_3$, CF$_2$CF$_3$ or CF$_2$CF$_2$CF$_3$ has previously been reported but these complexes were found to be practically insoluble in water. See Cowens et al., *Int. J. of Mass Spectrometry and Ion Physics*, 48, 177–180 (1983).

The complexes wherein X in Formula I is carboxylate may be prepared by acylation of the intermediate formed by hydrogen peroxide oxidation of [Pt(H$_2$O)$_2$(R$^1$NH$_2$) (R$^2$)$^{2+}$] prepared in turn from PtI$_2$(R$^1$NH$_2$) (R$^2$) and silver nitrate.

As noted, the complexes of the invention demonstrate antitumor activity when administered orally for the treatment of malignant tumors. Accordingly, the complexes may be formulated into tablets, pills, capsules, sterile suspensions, solutions or the like suitable for oral administration. Conventional pharmaceutical carriers, additives, binders, and/or excipients may also be used.

The invention is illustrated, but not limited, by the following examples wherein "c-t-c" is used as an abbreviation for "cis-trans-cis" in order to identify the stereochemistry of ligands around the octahedral Pt center when grouped pairwise in the order written and "c-C$_x$H$_y$" is used to refer to a cyclic alkyl radical with the ring size specified by the subscript x.

EXAMPLE 1 c-t-c-PtCl$_2$(O$_2$CCH$_3$)$_2$(NH$_3$)(c-C$_5$H$_9$NH$_2$) Compound No. 33

0.31 g of c-t-c-PtCl$_2$ (OH)$_2$ (NH$_3$) (c-C$_5$H$_9$NH$_2$) was stirred in 7 ml of acetic anhydride until the solid dissolved. The solution was chilled to 5° C. and the product crystallized. Addition of ether yielded additional product. The solid was collected, washed with ether and dried in vacuo. The yield was 0.33 g, 87% based on Pt. The product was recrystallized from hot ethyl acetate/hexane.

EXAMPLE 2 c-t-c-PtCl$_2$(O$_2$CCH$_3$)$_2$(NH$_3$)(n-C$_3$H$_7$NH$_2$) Compound No. 9

The product was synthesized by the method described in Example 1 but using c-t-c-PtCl$_2$(OH)$_2$(NH$_3$)(n-C$_3$H$_7$NH$_2$) in place of the Pt reactant of Example 1.

EXAMPLE 3 c-t-c-PtCl$_2$(O$_2$CCH$_2$CH$_3$)$_2$(NH$_3$)(n-C$_3$H$_7$NH$_2$) Compound No. 10

The product of this example was synthesized using propionic anhydride and 2 g of c-t-c-PtCl$_2$(OH)$_2$(n-C$_3$H$_7$NH$_2$)$_2$. The reaction yielded 0.87 g product (33%).

EXAMPLE 4 c-t-c-PtCl$_2$(O$_2$CCH$_2$CH$_3$)$_2$(NH$_3$)(t-C$_4$H$_9$NH$_2$) Compound No. 23

The method described in Example 1 using propionic anhydride and 1 g of c-t-c-PtCl$_2$(OH)$_2$(NH$_3$)(t-C$_4$H$_9$NH$_2$) was repeated to yield 0.30 g product (23%).

EXAMPLE 5 c-t-c-PtCl$_2$(O$_2$CC(CH$_3$)$_3$)$_2$(i-C$_3$H$_7$NH$_2$)$_2$ Compound No. 6

The product was synthesized by the method described in Example 1 using pivalic anhydride and 1 g of c-t-c-PtCl$_2$(OH)$_2$(i-C$_3$H$_7$NH$_2$)$_2$ and yielding 0.82 g of product (59%).

EXAMPLE 6 c-t-c-PtCl$_2$(O$_2$CCH$_2$CH$_2$CH$_3$)$_2$(i-C$_3$H$_7$NH$_2$)$_2$ Compound No. 5

The product was synthesized by the method described in the foregoing examples and precipitated out of solution by adding excess hexane and cooling to 0° C. The reactants, butyric anhydride and 1 g of c-t-c-PtCl$_2$(OH)$_2$(i-C$_3$H$_7$NH$_2$)$_2$, yielded 0.85 g product (64%).

EXAMPLE 7 c-t-c-PtCl$_2$(O$_2$CC$_6$H$_5$)$_2$(i-C$_3$H$_7$NH$_2$)$_2$ Compound No. 7 c-t-c-PtCl$_2$(OH)$_2$(i-C$_3$H$_7$NH$_2$)$_2$ (2 g 0.0048 mole) was dissolved in benzoic anhydride (10.82 g), pyridine (0.15 mL) and toluene (5 mL). The product, which precipitated after several hours, was collected, washed with copious amounts of ether to dissolve the excess benzoic anhydride, and dried in vacuo. The product was recrystallized from hot ethyl acetate/hexane. The reaction yielded 1.25 g (41%).

EXAMPLE 8 c-t-c-PtCl$_2$(O$_2$CC$_2$H$_5$)$_2$(i-C$_3$H$_7$NH$_2$)$_2$ Compound No. 4

1 g of c-t-c-PtCl$_2$(OH)$_2$(i-C$_3$H$_7$NH$_2$)$_2$ was suspended in dichloromethane (50 ml) and triethylamine (0.72 g, 3 eq). Propionyl chloride (0.63 ml, 3 eq) in CH$_2$Cl$_2$ (5 ml) was added dropwise. After 15 min stirring, water (20 ml) was added, the mixture filtered and the organic layer washed with water (2×20 ml), dried over MgSO$_4$ and evaporated to dryness in vacuo. The residue was recrystallized from ethyl acetate/ether. The yield of c-t-c-PtCl$_2$(O$_2$CC$_2$H$_5$)$_2$(i-C$_3$H$_7$NH$_2$)$_2$ was 0.18 g, 14%.

EXAMPLE 9 c-t-c-PtCl$_2$(O$_2$CCH(CH$_3$)CH$_2$CH$_3$)$_2$NH$_3$(c-C$_6$H$_{11}$NH$_2$) Compound No. 4

(S)-(+)-2-methylbutyric acid (0.982 g) and triethylamine (0.971 g) were dissolved in dry dimethylacetamide (10 ml) and cooled to 0° C. Isobutylchloroformate (1.3 g) in dimethylacetamide (2 ml) was added dropwise to the solution which was stirred at <4° C. for 2 hours c-t-c-PtCl$_2$(OH)$_2$NH$_3$(c-C$_6$H$_{11}$NH$_2$) (1 g) suspended in dimethylacetamide (10 ml) was added and the mixture stirred 24 hours at room temperature. Water (10 ml) and CH$_2$Cl$_2$ (10 ml) were added, the organic layer collected and the aqueous layer extracted with further CH$_2$Cl$_2$ (10 ml). The combined organics were washed with saturated aqueous NaHCO$_3$ (2×10 ml) and the solvent removed in vacuo. The resulting orange oil was crystalized from ethyl acetate/ether. The yellow crystals (500 mg) of c-t-c-PtCl$_2$(O$_2$CCH(CH)$_3$CH$_2$CH$_3$)$_2$NH$_3$(c-C$_6$H$_{11}$NH$_2$) were shown by microanalysis to contain 1 mole of dimethylacetamide/Pt. The presence of dimethylacetamide was confirmed by IR spectroscopy.

EXAMPLE 10 c-t-c-PtCl$_2$(O$_2$CH)$_2$NH$_3$(c-C$_6$H$_{11}$NH$_2$) Compound No. 37 c-t-c-PtCl$_2$(OH)$_2$NH$_3$(c-C$_6$H$_{11}$NH$_2$) (140 mg) was dissolved in formic acid (96%, 2 ml) and heated to 50°. After 1 hour the solution was cooled to room temperature, the resulting white solid filtered off, washed with water (3×5 ml) and dried to give c-t-c-PtCl$_2$(O$_2$CH)$_2$NH$_3$(c-C$_6$H$_{11}$NH$_2$) (80 mg, 50%).

EXAMPLE 11 c-t-c-PtBr$_2$(O$_2$C-n-C$_3$H$_7$)$_2$NH$_3$(c-C$_6$H$_{11}$NH$_2$) Compound No. 66 cis-PtI$_2$(NH$_3$)(c-C$_6$H$_{11}$NH$_2$) (8.01 g) was suspended in a mixture of water (50 ml) and ethanol (10 ml). Silver nitrate (4.7 g, 1.95 eq) was added and the mixture stirred in the dark overnight. The precipitated silver iodide was removed by filtration and HBr (48% aqueous solution, 30 ml) added. After stirring for 1.5 hr the yellow cis-PtBr$_2$(NH$_3$)(c-C$_6$H$_{11}$NH$_2$) (6.9 g) was collected by filtration and dried.

The dibromo complex (6.9 g) was oxidized by treatment with H$_2$O$_2$ 3 eq/Pt in water (15 ml) and acetone (10 ml) for 3 hr at 60°–70° C. On cooling PtBr$_2$(OH)$_2$NH$_3$(c-C$_6$H$_{11}$NH$_2$) crystallized out and was collected by filtration, washed with water and dried. Yield 5.05 g, 67%. This compound (1.5 g) was stirred in butyric anhydride (15 ml) for 3 days at room temperature to give a pale yellow solution which was partitioned between dichloromethane (20 ml) and water (20 ml). The organic layer was washed with saturated aqueous sodium bicarbonate, dried (MgSO$_4$) and the solvent removed in vacuo. The resulting yellow oil was triturated with hexane to give c-t-c-PtBr$_2$(O$_2$C-n-C$_3$H$_7$)$_2$NH$_3$(c-C$_6$H$_{11}$NH$_2$) (0.39 g, 20%) as a yellow powder.

EXAMPLE 12 c-t-c-PtCl$_2$(O$_2$CCH$_3$)(O$_2$C-n-CH$_3$H$_7$)NH$_3$(c-C$_6$H$_{11}$NH$_2$) Compound No. 72

3.35 g c-t-c-PtCl$_2$(OH)$_2$NH$_3$(c-C$_6$H$_{11}$NH$_2$) was stirred in a mixture of dichloromethane (15 ml) and diethylether (15 ml). A mixture of butyric anhydride (2.29 g, 1.8 eq/Pt and acetic anhydride (0.164 g, 0.2 eq/Pt) was added and the reaction stirred for 20 hours. The resulting white solid was collected by filtration, washed with ether and dried. The yield was 3.30 g. Thin layer chromatography (TLC) (silica gel, eluting with ethylacetate:dichloromethane, 1:1) showed the solid to be a mixture of two compounds. 0.9 g of the above mixture was dissolved in 1:1 ethylacetate:dichloromethane and chromatographed on a silica column. The first compound eluted was c-t-c-PtCl$_2$(O$_2$C-n-C$_3$H$_7$)$_2$NH$_3$(c-C$_6$H$_{11}$NH$_2$) (450 mg). The second compound eluted (50 mg) was the desired product c-t-c-PtCl$_2$(O$_2$CCH$_3$)(O$_2$C-n-C$_3$H$_7$)NH$_3$(c-C$_6$H$_{11}$NH$_2$) confirmed by microanalysis, NMR and IR spectroscopy. TLC on this sample gave a single spot, Rf 0.3.

EXAMPLE 13 c-t-c-PtCl$_2$(O$_2$CCH$_3$)(O$_2$C-n-C$_4$H$_9$)(NH$_3$)(c-C$_6$H$_{11}$NH$_2$) Compound No. 73 c-t-c-PtCl$_2$(OH)$_2$(NH$_3$)(c-C$_6$H$_{11}$NH$_2$) was suspended in a mixture of dichloromethane (10 ml) ether (15 ml), valeric anhydride (1.8 eq/Pt) and acetic anhydride (1.2 eq/Pt) and stirred at room temperature. After 24 hours the solid was collected by filtration, washed with ether and stirred in dichloromethane (20 ml) for 30 min. Unreacted c-t-c-PtCl$_2$(OH)$_2$NH$_3$(c-C$_6$H$_{11}$NH$_2$) (0.65 g) was collected by filtration and the CH$_2$Cl$_2$ soluble fraction evaporated in vacuo. The residual oil (0.4 g) was chromatographed on a 7"×1" diameter column of silica eluting with 1:1 ethylacetate/dichloromethane. Three fractions were collected. The first, c-t-c-PtCl$_2$(O$_2$C-n-C$_4$H$_9$)$_2$(NH$_3$)(c-C$_6$H$_{11}$NH$_2$) (0.092 g) was shown to be identical with a sample of compound 42 prepared by acylation with pure valeric anhydride. The third fraction, c-t-c-PtCl$_2$(O$_2$CCH$_3$)$_2$(NH$_3$)(c-C$_6$H$_{11}$NH$_2$) (0.082 g) was identical to an authentic sample of compound 38. The intermediate fraction (0.168 g) was c-t-c-PtCl$_2$(O$_2$CCH$_3$)(O$_2$C-n-C$_4$H$_9$)(NH$_3$)(c-C$_6$H$_{11}$NH$_2$), confirmed by microanalysis, IR and NMR spectroscopy and was shown to be pure by TLC.

EXAMPLE 14 c-t-c-PtCl$_2$(O$_2$CNHCH$_3$)$_2$(NH$_3$)(t-C$_4$H$_9$NH$_2$) Compound No. 26 c-t-c-PtCl$_2$(OH)$_2$(NH$_3$)(t-C$_4$H$_9$NH$_2$) was stirred in n-methyl isocyanate (10 mL/g) for 2 hours. The product was collected, washed with ether and dried in vacuo. 1 g c-t-c-PtCl$_2$(OH)$_2$(NH$_3$)(t-C$_4$H$_9$NH$_2$) starting material yielded 1.26 g product (97%).

EXAMPLE 15 cis-Pt(O$_2$CCH$_3$)$_4$(NH$_3$)(i-C$_3$H$_7$NH$_2$) Compound No. 68

6.11 g cis-PtI$_2$(NH$_3$)(i-C$_3$H$_7$NH$_2$) was added to a stirred solution of AgNO$_3$ (3.86 g, 1.95 eq.) in water (10 ml). Stirring was continued for 1 hour and charcoal (approximately 200 mg) was added and stirred for 10 min. After filtration, H$_2$O$_2$ (30%, 20 ml) was added to the filtrate and the reaction mixture stirred for 72 hours at room temperature. Carbon black (1 g) was added, and the mixture was stirred overnight to remove excess H$_2$O$_2$. The carbon was removed by filtration and acetone (200 ml) was added to the filtrate. The reaction mixture was chilled (−20° C.) overnight. The resulting pale yellow solid was collected, washed with acetone and ether and dried in vacuo. This solid was added to acetic anhydride (20 ml) and potassium acetate (4 g) and the mixture stirred 24 hours at room temperature and then left one week before being poured into water (100 ml). The mixture was stirred 5 min and then extracted with chloroform (4×25 ml). The combined chloroform extracts were washed with saturated aq. $NaHCO_3$ (2×50 ml), saturated aq. NaCl (50 ml) and dried over $MgSO_4$. On rotary evaporation, some acetic anhydride remained, so ethanol (20 ml) was added, allowed to react for 5 min and removed. This process was repeated until all acetic anhydride was removed as ethyl acetate and acetic acid. The resulting oil was crystallized from ether/hexane yielding yellow needles, 0.57 g, 11% yield.

EXAMPLE 16 c-t-c-Pt(CBDCA)($O_2CCH_3$)$_2$($NH_3$)$_2$ Compound No. 69 c-Pt(CBDCA)($NH_3$)$_2$ (4.45 g) was heated at 80° for 10 min in a mixture of hydrogen peroxide (30.1, 20 ml). On cooling c-t-c-Pt(CBDCA)(OH)$_2$($NH_3$)$_2$ crystallized out. The white solid was filtered off, washed with water and dried. The yield was 3.38 g, 70%. c-t-c-Pt(CBDCA)(OH)$_2$($NH_3$)$_2$ (1 g) was suspended in acetic anhydride (10 ml) and stirred 48 hr at room temperature. Ether (20 ml) was added, and the white solid was collected by filtration, washed with ether, and dried to give c-t- -Pt(CBDCA)($O_2CCH_3$)$_2$($NH_3$)$_2$ (0.99 g, 82%).

(CBDCA = cyclobutane-1,1-dicarboxylate)

EXAMPLE 17 c-t-c-$PtCl_2$($O_2COC_2H_5$)$_2$$NH_3$($NH_2$-n-$C_3H_7$) Compound No. 8

A suspension of 1.25 g of c-t-c-$PtCl_2$(OH)$_2$$NH_3$($NH_2$-n-$C_3H_7$) is stirred in the dark at RT in 15 ml diethylpyrocarbonate until an IR of the solid no longer shows a PtOH stretch at 3520 cm$^{-1}$ (10 days). The solid product (1.1 g, 63% yield) was collected, washed with ether and dried.

Microanalytical data obtained for compounds representative of the invention are set out in Table 1:

TABLE 1

MICROANALYTICAL DATA

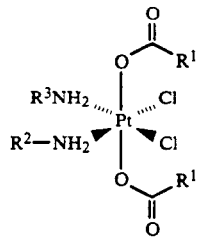

| Cmpd # | R$^1$ | R$^2$ | R$^3$ | % Calc. C | % Calc. H | % Calc. N | % Found C | % Found H | % Found N | Prepared According to Example # |
|---|---|---|---|---|---|---|---|---|---|---|
| 1 | $CH_3$ | H | H | 11.5 | 2.9 | 6.7 | 11.3 | 2.8 | 6.8 | 6 |
| 2 (a) | n-$C_3H_7$ | H | H | 19.5 | 4.5 | 5.7 | 19.1 | 4.0 | 5.7 | 6 |
| 3 | $CH_3$ | i-$C_3H_7$ | i-$C_3H_7$ | 23.9 | 4.8 | 5.6 | 23.7 | 4.8 | 5.5 | 6 |
| 4 | $C_2H_5$ | i-$C_3H_7$ | i-$C_3H_7$ | 27.2 | 5.3 | 5.3 | 27.3 | 5.3 | 5.2 | 6,8 |
| 5 | n-$C_3H_7$ | i-$C_3H_7$ | i-$C_3H_7$ | 30.1 | 5.8 | 5.0 | 30.3 | 5.8 | 5.0 | 6 |
| 6 | t-$C_4H_9$ | i-$C_3H_7$ | i-$C_3H_7$ | 32.8 | 6.2 | 4.8 | 32.5 | 6.1 | 4.9 | 5 |
| 7 | $C_6H_5$ | i-$C_3H_7$ | i-$C_3H_7$ | 38.4 | 4.5 | 4.5 | 38.5 | 4.4 | 4.5 | 7 |
| 8 | $OCH_3$ | i-$C_3H_7$ | i-$C_3H_7$ | 22.5 | 4.5 | 5.2 | 22.0 | 4.4 | 5.2 | 17 |
| 9 | $CH_3$ | H | n-$C_3H_7$ | 18.3 | 3.9 | 6.1 | 18.4 | 3.9 | 5.8 | 2 |
| 10 | $C_2H_5$ | H | n-$C_3H_7$ | 22.1 | 4.5 | 5.7 | 22.0 | 4.5 | 5.7 | 3 |
| 11 | n-$C_3H_7$ | H | n-$C_3H_7$ | 25.6 | 5.1 | 5.4 | 25.8 | 5.1 | 5.5 | 6 |
| 12 | n-$C_4H_9$ | H | n-$C_3H_7$ | 28.7 | 5.6 | 5.2 | 28.7 | 5.5 | 5.1 | 6 |
| 13 | $C_6H_5$ | H | n-$C_3H_7$ | 34.9 | 3.8 | 4.8 | 35.6 | 4.2 | 4.8 | 7 |
| 14 | $C_2H_5$ | H | n-$C_3H_7$ | 20.8 | 4.3 | 5.4 | 20.5 | 4.0 | 5.3 | 6 |
| 15 | $NHCH_3$ | n-$C_3H_7$ | n-$C_3H_7$ | 17.2 | 4.1 | 11.4 | 17.4 | 4.2 | 11.5 | 14 |
| 16 | $NHC_6H_4$-p-$CH_3$ | H | n-$C_3H_7$ | 29.6 | 3.7 | 7.3 | 30.2 | 3.8 | 7 | 14 |
| 17 | $OCH_2CH_3$ | H | n-$C_3H_7$ | 20.8 | 4.3 | 5.4 | 20.5 | 4.0 | 5.3 | 17 |
| 18 | $CH_3$ | H | i-$C_3H_7$ | 18.3 | 3.9 | 6.1 | 18.2 | 3.8 | 6.0 | 6 |
| 19 | $CH_3$ | H | i-$C_4H_9$ | 26.3 | 4.3 | 5.9 | 20.6 | 4.2 | 5.7 | 6 |
| 20 | n-$C_3H_7$ | H | i-$C_4H_9$ | 27.2 | 5.3 | 5.3 | 27.2 | 5.4 | 5.4 | 6 |
| 21 | n-$C_4H_9$ | H | i-$C_4H_9$ | 30.1 | 5.7 | 5.0 | 30.0 | 5.9 | 5.0 | 6 |
| 22 | $CH_3$ | H | t-$C_4H_9$ | 20.3 | 4.2 | 5.9 | 19.9 | 4.1 | 5.7 | 6 |
| 23 | $C_2H_5$ | H | t-$C_4H_9$ | 23.9 | 4.8 | 5.6 | 24.6 | 4.9 | 5.5 | 4 |
| 24 | n-$C_3H_7$ | H | t-$C_4H_9$ | 27.1 | 5.3 | 5.3 | 26.7 | 5.0 | 5.2 | 6 |
| 25 | n-$C_4H_9$ | H | t-$C_4H_9$ | 30.1 | 5.7 | 5.0 | 29.4 | 5.5 | 4.9 | 6 |
| 26 | $NHCH_3$ | H | t-$C_4H_9$ | 19.1 | 4.4 | 11.1 | 19.0 | 4.4 | 11.2 | 14 |
| 27 | $CH_3$ | H | $CH_2C(CH_3)_3$ | 22.1 | 4.5 | 5.7 | 22.2 | 4.5 | 5.6 | 6 |
| 28 | n-$C_3H_7$ | H | $CH_2C(CH_3)_3$ | 28.7 | 5.6 | 5.2 | 28.9 | 5.6 | 5.1 | 6 |
| 29 | $CH_3$ | H | c-$C_4H_7$ | 20.3 | 3.9 | 5.9 | 19.9 | 3.8 | 6.1 | 6 |
| 30 | $C_2H_5$ | H | c-$C_4H_7$ | 24.0 | 4.4 | 5.6 | 23.9 | 4.5 | 5.6 | 6 |
| 31 | n-$C_3H_7$ | H | c-$C_4H_7$ | 27.3 | 4.9 | 5.3 | 27.1 | 4.9 | 5.2 | 6 |
| 32 | H | H | c-$C_5H_9$ | 18.3 | 3.5 | 6.1 | 18.6 | 3.7 | 6.2 | 10 |
| 33 | $CH_3$ | H | c-$C_5H_9$ | 22.3 | 3.5 | 5.8 | 22.4 | 4.1 | 5.5 | 1 |
| 34 | $C_2H_5$ | H | c-$C_5H_9$ | 25.7 | 4.7 | 5.5 | 25.8 | 4.5 | 5.2 | 6 |
| 35 | n-$C_3H_7$ | H | c-$C_5H_9$ | 28.8 | 5.2 | 5.2 | 28.6 | 5.2 | 5.0 | 6 |
| 36 | $C_6H_5$ | H | c-$C_5H_9$ | 37.4 | 4.0 | 4.6 | 38.6 | 3.6 | 4.1 | 7 |
| 37 | H | H | c-$C_6H_{11}$ | 20.3 | 3.8 | 5.9 | 20.4 | 3.7 | 5.9 | 10 |
| 38 | $CH_3$ | H | c-$C_6H_{11}$ | 24.0 | 4.4 | 5.6 | 24.4 | 4.4 | 5.3 | 6 |
| 39 | $C_2H_5$ | H | c-$C_6H_{11}$ | 27.3 | 5.0 | 5.3 | 27.8 | 4.9 | 5.2 | 6 |
| 40 | n-$C_3H_7$ | H | c-$C_6H_{11}$ | 30.2 | 5.4 | 5.0 | 30.3 | 5.4 | 5.0 | 6 |

TABLE 1-continued
MICROANALYTICAL DATA

| # | | | | | | | | | | |
|---|---|---|---|---|---|---|---|---|---|---|
| 41 | i-$C_3H_7$ | H | c-$C_6H_{11}$ | 30.2 | 5.4 | 5.0 | 30.1 | 5.4 | 5.0 | 6 |
| 42 | n-$C_4H_9$ | H | c-$C_6H_{11}$ | 32.9 | 5.8 | 4.8 | 32.7 | 5.7 | 4.7 | 6 |
| 43 (b) | s-$C_4H_9$ | H | c-$C_6H_{11}$ | 35.8 | 6.4 | 6.3 | 35.6 | 6.5 | 6.2 | 9 |
| 44 | t-$C_4H_9$ | H | c-$C_6H_{11}$ | 32.9 | 5.8 | 4.8 | 32.7 | 5.8 | 4.7 | 6 |
| 45 | n-$C_9H_{19}$ | H | c-$C_6H_{11}$ | 43.1 | 7.5 | 3.9 | 42.9 | 7.6 | 3.8 | 8 |
| 46 (c) | c-$C_3H_5$ | H | c-$C_6H_{11}$ | 33.5 | 5.3 | 4.6 | 33.3 | 5.2 | 4.5 | 8 |
| 47 | c-$C_6H_{11}$ | H | c-$C_6H_{11}$ | 37.7 | 6.0 | 4.4 | 38.0 | 6.0 | 4.7 | 8 |
| 48 | trans-$CHCHCH_3$ | H | c-$C_6H_{11}$ | 30.4 | 4.7 | 5.1 | 31.0 | 4.9 | 4.8 | 6 |
| 49 (a) | $CH_2C_6H_5$ | H | c-$C_6H_{11}$ | 39.4 | 4.8 | 4.2 | 39.3 | 4.7 | 4.3 | 8,9 |
| 50 | $CH_2$-c-$C_6H_{11}$ | H | c-$C_6H_{11}$ | 39.8 | 6.4 | 4.2 | 40.0 | 6.4 | 4.3 | 8 |
| 51 | $CH_2Cl$ | H | c-$C_6H_{11}$ | 21.1 | 3.5 | 4.9 | 21.4 | 3.6 | 4.8 | 6 |
| 52 | $CH_2CH_2Cl$ | H | c-$C_6H_{11}$ | 25.9 | 4.4 | 4.5 | 25.6 | 4.4 | 4.8 | 8 |
| 53 | $NHCH_2CH_3$ | H | c-$C_6H_{11}$ | 25.8 | 5.0 | 10.0 | 25.9 | 4.9 | 9.8 | 14 |
| 54 | $NHCH_2CH_3$ | H | c-$C_5H_9$ | 24.3 | 4.8 | 10.3 | 24.0 | 4.6 | 10.2 | 14 |
| 55 | $CH_3$ | H | c-$C_7H_{13}$ | 25.5 | 4.6 | 5.4 | 25.3 | 4.6 | 5.1 | 6 |
| 56 | $C_2H_5$ | H | c-$C_7H_{13}$ | 28.6 | 5.1 | 5.1 | 28.9 | 5.2 | 5.0 | 6 |
| 57 | n-$C_3H_7$ | H | c-$C_7H_{13}$ | 31.4 | 5.6 | 4.9 | 31.8 | 5.7 | 4.8 | 6 |
| 58 | $CH_3$ | H | n-$C_{10}H_{21}$ | 30.1 | 5.8 | 5.0 | 30.2 | 5.7 | 5.0 | 6 |
| 59 | $CH_3$ | H | $C_6H_5$ | 24.3 | 3.2 | 5.7 | 24.0 | 3.1 | 5.6 | 6 |
| 60 (d) | $C_6H_4$-4-$OCH_3$ | H | c-$C_6H_{11}$ | 38.1 | 4.2 | 4.0 | 37.8 | 4.4 | 4.1 | 9 |
| 61 (e) | $C_6H_4$-4-$NO_2$ | H | c-$C_6H_{11}$ | 39.0 | 4.8 | 7.0 | 39.0 | 4.4 | 7.0 | 9 |
| 62 | $CH_2OCH_3$ | H | c-$C_6H_{11}$ | 25.7 | 4.7 | 5.0 | 25.6 | 4.7 | 5.0 | 6 |
| 63 | $CH_3$ | H | (f) | 26.4 | 4.8 | 4.8 | 26.7 | 4.7 | 4.7 | 6 |

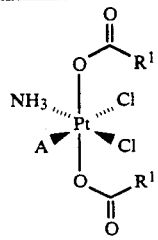

| Cmpd # | $R^1$ | A | % Calc. C | % Calc. H | % Calc. N | % Found C | % Found H | % Found N | Prepared According to Example # |
|---|---|---|---|---|---|---|---|---|---|
| 64 | $CH_3$ | pyridine | 22.5 | 2.9 | 5.8 | 22.4 | 2.9 | 5.8 | 1 |

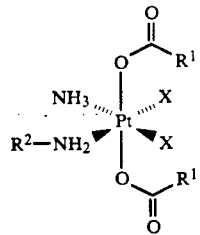

| Cmpd # | $R^1$ | $R^2$ | X | % Calc. C | % Calc. H | % Calc. N | % Found C | % Found H | % Found N | Prepared According to Example # |
|---|---|---|---|---|---|---|---|---|---|---|
| 66 | n-$C_3H_7$ | c-$C_6H_{11}$ | Br | 26.1 | 4.7 | 4.3 | 26.2 | 4.5 | 4.4 | 11 |
| 67 | $CH_3$ | H | $O_2CCH_3$ | 20.7 | 3.4 | 6.0 | 20.9 | 3.4 | 4.8 | 15 |
| 68 | $CH_3$ | i-$C_3H_7$ | $O_2CCH_3$ | 25.0 | 4.7 | 5.5 | 25.6 | 4.4 | 5.5 | 15 |

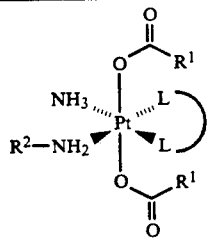

| Cmpd # | $R^1$ | $R^2$ | L⌒L | % Calc. C | % Calc. H | % Calc. N | % Found C | % Found H | % Found N | Prepared According to Example # |
|---|---|---|---|---|---|---|---|---|---|---|
| 69 | $CH_3$ | H | CBCDA (g) | 24.5 | 3.7 | 5.7 | 24.1 | 3.2 | 5.5 | 16 |
| 70 (d) | $CH_3$ | i-$C_4H_9$ | CBCDA (g) | 30.3 | 4.9 | 5.1 | 30.0 | 4.6 | 4.9 | 16 |
| 71 | $CH_3$ | c-$C_6H_{11}$ | oxalate | 27.9 | 4.3 | 5.4 | 27.9 | 4.4 | 5.1 | 16 |

TABLE 1-continued
MICROANALYTICAL DATA

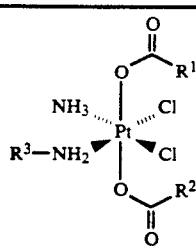

| Cmpd # | R[1] | R[2] | R[3] | % Calc. C | % Calc. H | % Calc. N | % Found C | % Found H | % Found N | Prepared According to Example # |
|---|---|---|---|---|---|---|---|---|---|---|
| 72 | $CH_3$ | n-$C_3H_7$ | C—$C_6H_{11}$ | 27.3 | 5.0 | 5.3 | 27.3 | 4.7 | 5.3 | 12 |
| 73 | $CH_3$ | n-$C_4H_9$ | C—$C_6H_{11}$ | 28.8 | 5.2 | 5.2 | 29.0 | 5.2 | 5.1 | 13 |

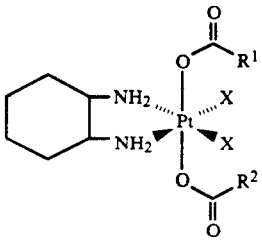

| Cmpd # | R[1] | R[2] | X | % Calc. C | % Calc. H | % Calc. N | % Found C | % Found H | % Found N | Prepared According to Example # |
|---|---|---|---|---|---|---|---|---|---|---|
| 74 | $CH_3$ | $CH_3$ | Cl | 24.1 | 4.1 | 5.6 | 24.4 | 4.1 | 6.2 | 1 |

(a) Contains 1 $H_2O$ of crystallization per Pt complex.
(b) Contains 1 dimethylacetamide of crystallization per Pt complex.
(c) Contains 1 acetone of crystallization per Pt complex.
(d) Contains ½ $H_2O$ of crystallization per Pt complex.
(e) Contains 1 hexane of crystallization per Pt complex.

(f) $CH_2CH(CH_2)_2CH(CO_2CH_3)CH_2CH_2$ (bridged)
(g) CBCDA = 1,1-cyclobutane dicarboxylate.

Complexes according to the invention were tested for antitumor activity using ADJ/PC6 tumor in mice. The complexes were administered parenterally (I.P.) or orally (P.O.). $LD_{50}$ and $ED_{90}$ values in mg/kg were determined with the results shown in Table 2:

TABLE 2
ANTITUMOR ACTIVITY IN ADJ/PC6

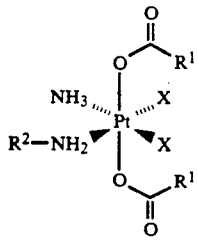

| Cmpd # | R[1] | R[2] | X | I.P. $LD_{50}$ | I.P. $ED_{90}$ | I.P. TI | P.O. $LD_{50}$ | P.O. $ED_{90}$ | P.O. TI |
|---|---|---|---|---|---|---|---|---|---|
| 1 | $CH_3$ | H | Cl | 35 | 9.2 | 3.8 | 142 | 21.5 | 6.6 |
| 8 | $CH_3$ | n-$C_3H_7$ | Cl | 35 | 3.1 | 11.3 | 235 | 18 | 13.1 |
| 9 | $C_2H_5$ | n-$C_3H_7$ | Cl | 41.5 | 5.6 | 7.4 | 118 | 8.6 | 13.7 |
| 10 | n-$C_3H_7$ | n-$C_3H_7$ | Cl | 17.5 | 5.4 | 3.2 | 140 | 5.2 | 26.9 |
| 11 | n-$C_4H_9$ | n-$C_3H_7$ | Cl | 15 | 3.5 | 4.3 | 141 | 8.4 | 16.8 |
| 17 | $CH_3$ | i-$C_4H_9$ | Cl | 71 | 2.7 | 26.3 | 330 | 14.5 | 22.8 |
| 18 | n-$C_3H_7$ | i-$C_4H_9$ | Cl | 17.5 | 3.0 | 5.9 | 240 | 3.1 | 77 |
| 21 | $C_2H_5$ | t-$C_4H_9$ | Cl | 17.5 | 5.5 | 3.0 | >200 | 10.3 | >19.4 |
| 24 | $NHCH_3$ | t-$C_4H_9$ | Cl | 42 | 4.4 | 9.5 | >800 | 22 | >36 |
| 25 | $CH_3$ | $CH_2C(CH_3)_3$ | Cl | | | | 280 | 29.5 | 9 |
| 26 | n-$C_3H_7$ | $CH_2C(CH_3)_3$ | Cl | 17.5 | 8.2 | 2.1 | 480 | 11.5 | 42 |
| 27 | $CH_3$ | c-$C_4H_7$ | Cl | 30.5 | 2.3 | 13.3 | 280 | 7.0 | 40 |
| 31 | $CH_3$ | c-$C_5H_9$ | Cl | 42 | 0.94 | 44.6 | 280 | 4.8 | 58.3 |
| 32 | $C_2H_5$ | c-$C_5H_9$ | Cl | 17.5 | 1.25 | 14.0 | 120 | 4.1 | 29.3 |

TABLE 2-continued

ANTITUMOR ACTIVITY IN ADJ/PC6

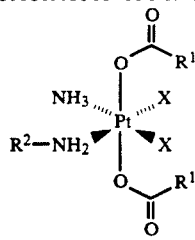

| Cmpd # | R¹ | R² | X | I.P. LD$_{50}$ | I.P. ED$_{90}$ | TI | P.O. LD$_{50}$ | P.O. ED$_{90}$ | TI |
|---|---|---|---|---|---|---|---|---|---|
| 33 | n-C$_3$H$_7$ | c-C$_5$H$_9$ | Cl | 8.7 | 2.7 | 3.2 | 141 | 5.2 | 27.1 |
| 36 | CH$_3$ | c-C$_6$H$_{11}$ | Cl | 30 | 5.7 | 5.3 | 330 | 5.8 | 56.9 |
| 37 | C$_2$H$_5$ | c-C$_6$H$_{11}$ | Cl | 17.5 | 2.8 | 6.3 | 240 | 7.0 | 34.3 |
| 38 | n-C$_3$H$_7$ | c-C$_6$H$_{11}$ | Cl | 15.3 | 2.5 | 6.2 | 280 | 5.2 | 53.9 |
| 63 | CH$_3$ | H | O$_2$CCH$_3$ | >200 | — | — | | | |
| 64 | CH$_3$ | i-C$_3$H$_7$ | O$_2$CCH$_3$ | 280 | 14.5 | 19.3 | | | |

The T.I. values indicate useful activity for the complexes, particularly for oral administration where the T.I. values were significantly higher than for parenteral (I.P.) administration.

It will be appreciated that various modifications may be made in the invention described herein. Hence, the scope of the invention is defined in the following claims wherein:

What is claimed is:

1. A Pt(IV) anti-tumor complex of the formula

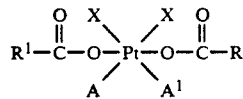

wherein A and A¹ are individually selected from the group consisting of NH$_3$ and an amino group of 1 to 10 carbon atoms, with the proviso that when both A and A¹ are amino groups, at least one is an amino group of 1 to 3 carbon atoms; both X groups are the same and are Cl or Br; R and R¹ are individually selected from the group consisting of C$_1$–C$_{10}$ alkyl, cycloalkyl, aryl, aralkyl of 3 to 7 carbon atoms, alkoxy, alkenyl, alkylamino of 1 to 6 carbon atoms wherein the group is joined to the carbonyl through the hetero-atom in the case of alkoxy and alkylamino, and H; such that the X groups are cis to each other and the CO$_2$R and CO$_2$R¹ groups are trans to each other.

2. A Pt(IV) complex according to claim 1 wherein X is Cl, A is NH$_3$, A' is a cycloalkylamine and R and R¹ are C$_1$–C$_7$ alkyl.

3. A Pt(IV) complex according to claim 2 wherein A' is cyclopentylamine or cyclohexylamine and R and R¹ are both propyl.

4. A Pt(IV) complex according to claim 1 wherein X is Cl, A is NH$_3$, A' is an alkylamine and R and R¹ are alkyl, alkylamino or alkoxy, of 1 to 6 carbon atoms.

5. A Pt(IV) complex according to claim 1 wherein X is Cl, A and A' are both alkylamine and R and R¹ are alkyl, of 1 to 6 carbon atoms.

6. A Pt(IV) complex according to claim 1 wherein X is a monocarboxylate or a bidentate dicarboxylate, R and R¹ are both alkyl of 1 to 6 carbon atoms, A is NH$_3$ and A' is alkylamino.

* * * * *